(12) United States Patent
Kuroda et al.

(10) Patent No.: US 7,541,363 B2
(45) Date of Patent: Jun. 2, 2009

(54) MICROCRYSTAL

(75) Inventors: Kazutoshi Kuroda, Ichikawa (JP); Noboru Aoki, Numazu (JP); Toshiro Ochiai, Sunto-gun (JP); Akihiro Uchida, Sunto-gun (JP); Yasuhiro Ishikawa, Sunto-gun (JP); Makoto Kigoshi, Sunto-gun (JP); Eiji Hayakawa, Sunto-gun (JP); Kazuki Asanome, Sunto-gun (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 190 days.

(21) Appl. No.: 10/554,511

(22) PCT Filed: May 7, 2004

(86) PCT No.: PCT/JP2004/006495

§ 371 (c)(1),
(2), (4) Date: Oct. 26, 2005

(87) PCT Pub. No.: WO2004/099207

PCT Pub. Date: Nov. 18, 2004

(65) Prior Publication Data

US 2006/0205745 A1    Sep. 14, 2006

(30) Foreign Application Priority Data

May 9, 2003    (JP)    .............................. 2003-131417

(51) Int. Cl.
C07D 473/06    (2006.01)
A61K 31/522    (2006.01)

(52) U.S. Cl. .................................. 514/263.34; 544/267
(58) Field of Classification Search .................. None
See application file for complete search history.

(56) References Cited

U.S. PATENT DOCUMENTS

| | | | | |
|---|---|---|---|---|
| 5,543,415 A | * | 8/1996 | Suzuki et al. | 514/263.24 |
| 5,587,378 A | | 12/1996 | Suzuki et al. | 514/264 |
| 6,254,889 B1 | | 7/2001 | Kigoshi et al. | 424/487 |
| 2006/0029663 A1 | * | 2/2006 | Uchida et al. | 424/464 |

FOREIGN PATENT DOCUMENTS

JP    09040652 A    *    2/1997

OTHER PUBLICATIONS

Abstract for JP 9040652 (Feb. 1997).

* cited by examiner

*Primary Examiner*—Mark L Berch
(74) *Attorney, Agent, or Firm*—Fitzpatrick, Cella, Harper & Scinto

(57) ABSTRACT

Microcrystals of (E)-8-(3,4-dimethoxystyryl)-1,3-diethyl-7-methyl-3,7-dihydro-1H-purine-2,6-dione having an average particle size of less than 50 μm; microcrystals of (E)-8-(3,4-dimethoxystyryl)-1,3-diethyl-7-methyl-3,7-dihydro-1H-purine-2,6-dione having an average particle size of less than 50 μm and a crystallinity of 20% or more or the like, which possess excellent solubility, stability, bioavailability, dispersing property in a pharmaceutical formulation; and the like are provided. A solid pharmaceutical formulation which is characterized by comprising the same is also provided.

5 Claims, 2 Drawing Sheets

MICROCRYSTAL

TECHNICAL FIELD

The present invention relates to crystals of (E)-8-(3,4-dimethoxystyryl)-1,3-diethyl-7-methyl-3,7-dihydro-1H-purine-2,6-dione (hereinafter, referred to as Compound 1) and also to a solid pharmaceutical formulation comprising the crystals.

BACKGROUND ART

Compound 1 shows an adenosine $A_2$ receptor antagonistic activity and is useful for the treatment of various diseases induced by hyperactivity of adenosine $A_2$ receptor such as Parkinson disease, senile dementia, depression, asthma and osteoporosis (European Patent No. 0,590,919; Japanese Published Unexamined Patent Application No. 040,652/97). It is known that xanthine derivatives including Compound 1 are used as a powder by pulverization for inhalation administration (European Patent No. 0,590,919). Crystals of Compound 1 have been known as well (Japanese Published Unexamined Patent Application No. 040,652/97). Crystals of Compound 1 synthesized by the process disclosed in the above citations have characteristics that (1) the solubility thereof in water is low and that (2) the form thereof is needle-like where a short diameter is several μm and a long diameter is not less than several hundred μm, and therefore, there are problems that, during the operation of steps for preparing pharmaceutical formulations, crystals of Compound 1 are aggregated. It has been said that drugs having low solubility in water generally have low bioavailability because of low solubility and slow dissolving velocity in digestive tracts. Also with regard to Compound 1, enhancement in its solubility, dissolving velocity or the like, for improvement of bioavailability and the like are demanded. On the other hand, aggregation of crystals of Compound 1, which takes place during the operations of the steps for preparing pharmaceutical formulations, affects on fluidity of crystals of Compound 1 and additives. Therefore, there are problems in view of handling of crystals of Compound 1 in the steps for preparing pharmaceutical formulations and in view of dispersibility of Compound 1 in the solid formulations. It is also known that Compound 1 is unstable particularly under light and a double bond moiety (vinylene moiety) in its structure is apt to be isomerized [*Bioorg. Med. Chem. Lett.*, volume 7, pages 2349-2352 (1997)], and careful attention is needed for handling in preparing the pharmaceutical formulations comprising Compound 1.

DISCLOSURE OF THE INVENTION

An object of the present invention is to provide crystals of Compound 1, which possess, for example, excellent solubility, stability, bioavailability, dispersing property in a pharmaceutical formulation or the like, and to provide solid pharmaceutical formulations comprising the crystals.

The present invention relates to the following (1) to (13).

(1) A microcrystal of (E)-8-(3,4-dimethoxystyryl)-1,3-diethyl-7-methyl-3,7-dihydro-1H-purine-2,6-dione represented by the following formula

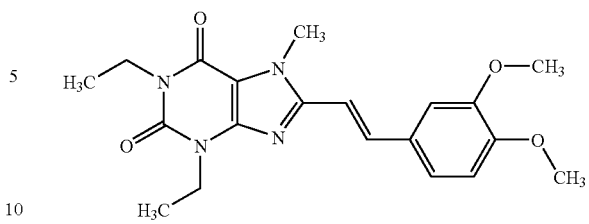

which has an average particle size of less than 50 μm.

(2) The microcrystal according to the above (1), wherein the average particle size of a microcrystal of (E)-8-(3,4-dimethoxystyryl)-1,3-diethyl-7-methyl-3,7-dihydro-1H-purine-2,6-dione is 0.5 to 20 μm.

(3) The microcrystal of (E)-8-(3,4-dimethoxystyryl)-1,3-diethyl-7-methyl-3,7-dihydro-1H-purine-2,6-dione according to the above (1) or (2), wherein a crystallinity thereof is 20% or more.

(4) The microcrystal of (E)-8-(3,4-dimethoxystyryl)-1,3-diethyl-7-methyl-3,7-dihydro-1H-purine-2,6-dione according to the above (1) or (2), wherein a crystallinity thereof is 30% or more.

(5) The microcrystal of (E)-8-(3,4-dimethoxystyryl)-1,3-diethyl-7-methyl-3,7-dihydro-1H-purine-2,6-dione according to the above (1) or (2), wherein a crystallinity thereof is 40% or more.

(6) A solid pharmaceutical formulation comprising the microcrystals described in any one of the above (1) to (5).

(7) A solid dispersion comprising crystals of (E)-8-(3,4-dimethoxystyryl)-1,3-diethyl-7-methyl-3,7-dihydro-1H-purine-2,6-dione having a crystallinity of 20% or more, and a dispersant.

(8) The solid dispersion according to the above (7), wherein the crystallinity of (E)-8-(3,4-dimethoxystyryl)-1,3-diethyl-7-methyl-3,7-dihydro-1H-purine-2,6-dione is 30% or more.

(9) The solid dispersion according to the above (7), wherein the crystallinity of (E)-8-(3,4-dimethoxystyryl)-1,3-diethyl-7-methyl-3,7-dihydro-1H-purine-2,6-dione is 40% or more.

(10) A solid pharmaceutical formulation comprising the solid dispersion described in any one of the above (7) to (9).

(11) A solid pharmaceutical formulation comprising (E)-8-(3,4-dimethoxystyryl)-1,3-diethyl-7-methyl-3,7-dihydro-1H-purine-2,6-dione having a crystallinity of 20% or more.

(12) The solid pharmaceutical formulation according to the above (11), wherein the crystallinity of (E)-8-(3,4-dimethoxystyryl)-1,3-diethyl-7-methyl-3,7-dihydro-1H-purine-2,6-dione is 30% or more.

(13). The solid pharmaceutical formulation according to the above (11), wherein the crystallinity of (E)-8-(3,4-dimethoxystyryl)-1,3-diethyl-7-methyl-3,7-dihydro-1H-purine-2,6-dione is 40% or more.

In the present specification, the term of "(E)-8-(3,4-dimethoxystyryl)-1,3-diethyl-7-methyl-3,7-dihydro-1H-purine-2,6-dione" (referred to as "Compound 1") means amorphous Compound 1, crystalline Compound 1 or a mixture of them. With regard to "Compound 1" used as the raw material, there is no limitation for a crystallinity thereof, an average particle size thereof and the like.

Although there is no particular limitation for the "microcrystal(s) of (E)-8-(3,4-dimethoxystyryl)-1,3-diethyl-7-methyl-3,7-dihydro-1H-purine-2,6-dione having an average particle size of less than 50 µm" (that is "microcrystal(s) of Compound 1") of the present invention so far as it is the crystalline Compound 1 having an average particle size of less than 50 µm, among them microcrystal(s) having an average particle size of 0.5 to 20 µm is/are preferable. The "microcrystal(s) of Compound 1" having a crystallinity of 20% or more is/are more preferable. Among them, the "microcrystal(s) of Compound 1" having a crystallinity of 30% or more is/are still more preferable and the "microcrystal(s) of Compound 1" having a crystallinity of 40% or more is/are most preferable. Incidentally, the average particle size thereof can be measured by using, for example, a laser diffraction/scattering particle size distribution analyzer (e.g., Mastersizer 2000, Ver. 2.00J; manufactured by Malvern Instruments), an image analyzer (e.g., Luzex® AP; manufactured by Nileco) or the like, and can be calculated as the mean of the particle size distribution. The crystallinity thereof can be calculated by measuring the integral intensity of the diffraction peak at a specific angle of diffraction 2θ by using a powder X-ray diffractmeter (e.g., JDX 8030; manufactured by Nippon Denshi).

Although there is no particular limitation for a preparation method of the "microcrystal(s) of Compound 1" of the present invention, these can be prepared by pulverization and/or sieving of "crystal(s) of (E)-8-(3,4-dimethoxystyryl)-1,3-diethyl-7-methyl-3,7-dihydro-1H-purine-2,6-dione having an average particle size of not less than 50 µm" (that is "crystal (s) of Compound 1"), which is/are obtained by the method described in, for example, European Patent No. 0,590,919, Japanese Published Unexamined Patent Application No. 040,652/97 or the like, or by the method similar thereto. The pulverization and the sieving may be appropriately carried out in combination several times. The pulverization can be carried out by a pulverizer generally used, such as a mortar, Mechanomill and a jet mill. In the pulverization, the pulverization conditions, such as the rotational speed of the pulverizer; the feed rate of the "crystal(s) of Compound 1"; the time required for pulverization; and the like, are appropriately controlled to obtain the "microcrystal(s) of Compound 1" having a desired average particle size and/or a desired crystallinity. Among them, the pulverization by the jet mill is preferable, and the "crystal(s) of Compound 1" can be pulverized, by feeding the "crystal(s) of Compound 1" at a rate of 10 to 1,000 g/min and under pressure of 0.01 to 1.0 MPa.

With regard to the solid pharmaceutical formulation of the present invention, comprising the "microcrystals of Compound 1", any formulations may be used so far as it is a solid pharmaceutical formulation comprising the above-described "microcrystals of Compound 1", and examples thereof include (a) formulations prepared by mixing the "microcrystals of Compound 1" obtained by the above-described methods and additives and preparing formulations;

(b) formulations prepared by mixing the "microcrystals of Compound 1" obtained by the above-described methods and additives, pulverizing and/or sieving the resulting mixture in a manner similar to those in the above-described methods for preparation of the "microcrystals of Compound 1" and then preparing formulations;

(c) formulations prepared by preparing a solid dispersion from "Compound 1" and a dispersant and then mixing the resulting solid dispersion and additives, followed by preparing formulations; and the like.

Incidentally, the "microcrystals of Compound 1" content of the solid pharmaceutical formulation of the present invention is preferably 0.001% to 80% or, more preferably, 0.1% to 50%.

The solid dispersion is a solid dispersion prepared from "Compound 1" or the "crystals of Compound 1" and a dispersant which can disperse the above. There is no particular limitation for the solid dispersion so far as the crystalline parts of Compound 1 in the solid dispersion have the average particle size, or the average particle size and the crystallinity of the "microcrystals of Compound 1" as described above. With regard to the dispersant, for example, polymer substances such as hydroxypropyl methylcellulose (HPMC), polyvinylpyrrolidone (PVP) and hydroxypropyl cellulose (HPC) are preferable. In addition, "Compound 1" or the "crystals of Compound 1" and the dispersant are combined in a combination ratio of preferably 1:0.1 to 1:5 (ratio by weight), more preferably 1:0.1 to 1:3 (ratio by weight). Although there is also no particular limitation for the process for producing the solid dispersions, these can be prepared by general methods such as a mixing/pulverizing method and a solvent method from "Compound 1" or "crystals of Compound 1", which is/are obtained by the method described, for example, in European Patent No. 0,590,919 or Japanese Published Unexamined Patent Application No. 040,652/97, or the method similar thereto, and the dispersant.

Examples of the mixing/pulverizing method include a method which consists of mixing the "crystals of Compound 1" and the dispersant in a blender or the like, and pulverizing by a generally used pulverizer such as a mortar, Mechanomill or a jet mill; or the like. For example, the rotational speed of the pulverizer, the feed rate of the "crystals of Compound 1", time required for pulverization and the like, are appropriately controlled to obtain the solid dispersion comprising the "microcrystals of Compound 1" having a desired average particle size, or a desired average particle size and a desired crystallinity. Among them, the pulverization by the jet mill is preferable.

Examples of the solvent method is a method which consists of dissolving or dispersing "Compound 1" or the "crystals of Compound 1" in an organic solvent with a dispersant and then removing the organic solvent by a general method under reduced pressure or ordinary pressure. Specifically, for example, a fluidized bed granulator, a stirring granulator, a spray granulator, a spray-drying granulator, a vacuum drying granulator and the like can be used and, if desired, a generally used pulverizer such as a mortar, Mechanomill or a jet mill is used may be combined therewith. There is no particular limitation for the organic solvent so far as it can dissolve "Compound 1" or the "crystals of Compound 1". Examples thereof include halogenated hydrocarbon such as dichloromethane, dichloroethane and chloroform; ketone such as acetone and methyl ethyl ketone; alcohol such as methanol and ethanol; ether such as tetrahydrofuran; esters such as ethyl acetate; and amide such as dimethylformamide and dimethylacetamide.

Examples of the additive include a vehicle, a binder, a disintegrator, a lubricant, a plasticizer, a surfactant, a coating agent, a colorant, a corrigent and an acidifying agent, and they, may be appropriately used depending upon the type of the preparation.

Examples of the vehicle include a sugar such as sucrose, glucose, sucrose, mannitol and lactose; starch such as corn starch and potato starch; and cellulose such as crystalline cellulose and microcrystalline cellulose.

Examples of the binder include polyvinyl alcohol, hydroxypropylcellulose, gelatin, methylcellulose, ethylcellulose and polyvinylpyrrolidone.

Examples of the disintegrator include starch such as corn starch and potato starch; agar; gelatin powder; crystalline cellulose; sodium alginate; and crospovidone.

Examples of the lubricant include magnesium stearate and talc.

Examples of the plasticizer include plant oil and glycerin.

Examples of the surfactant include sodium lauryl sulfate, polysorbate 80 and fatty acid esters.

Examples of the coating agent include sugar coating such as sucrose and hydroxypropylcellulose; and glue coating such as gelatin, glycerol and sorbitol.

Examples of the colorant include food dyes. Examples of the corrigent are sodium saccharide, aspartame and stevia. Examples of the acidifying agent include citric acid, malic acid and tartaric acid.

There is no particular limitation for the "crystal(s) of (E)-8-(3,4-dimethoxystyryl)-1,3-diethyl-7-methyl-3,7-dihydro-1H-purine-2,6-dione where crystallinity is 20% or more" (that is "crystal(s) of Compound 1 where crystallinity is not less than 20%") so far as it is the crystalline Compound 1 having a crystallinity of 20% or more. Among them, the crystalline Compound 1 having a crystallinity of 30% or more is preferable, and the crystalline Compound 1 having a crystallinity of 40% or more is more preferable. There is also no particular limitation for the process for producing the compound, and for example, the compound can be obtained by the method described in European Patent No. 0,590,919, Japanese Published Unexamined Patent Application No. 040,652/97 or the like, or by the method similar thereto.

With regard to the solid pharmaceutical formulation comprising the "crystals of Compound 1 having a crystallinity of 20% or more", any formulations may be used so far as it is a solid pharmaceutical formulation comprising the above-described "crystals of Compound 1 having a crystallinity of 20% or more". There is also no particular limitation for the process for producing the solid pharmaceutical formulations, and examples thereof include the same process as the above-described processes for producing the solid pharmaceutical formulations comprising the "microcrystals of Compound 1".

The solid dispersion comprising the "crystals of Compound 1 having a crystallinity of 20% or more" and a dispersant is a solid dispersion which is prepared from "Compound 1" or the "crystals of Compound 1", and a dispersant which can disperse it. There is no particular limitation for an average particle size thereof and the like so far as the crystalline parts of Compound 1 in the solid dispersion have a crystallinity of 20% or more. There is also no particular limitation for the process for producing the solid dispersions, and examples thereof include a process which is the same as the above-described process for producing solid dispersions comprising the "microcrystals of Compound 1" and a dispersant. With regard to the dispersant, for example, HPMC, PVP, HPC and the like are preferable. In addition, "Compound 1" or the "crystals of Compound 1" and the dispersant are combined in a combination ratio of preferably 1:0.1 to 1:5 (ratio by weight), more preferably 1:0.1 to 1:3 (ratio by weight)

Examples of the dosage form of the solid pharmaceutical formulation of the present invention include tablets such as sugar-coated tablets, diluted powders, granules, capsules, pills, troches and suspension liquids for oral application, and the formulations can be manufactured by combining the steps for preparing formulations, which have been well known in the technical field of pharmaceutics, such as a mixing step, a pulverizing step, a sieving step, a granulation step, a milling step, a tabletting step, a drying step, a capsule-filling step and a coating step.

The following Test Examples specifically illustrated effects of the present invention.

TEST EXAMPLE 1

Crystallinity of Compound 1 and Photostability

<Method for Preparing Samples>

As described below, solid dispersions were prepared from the "crystals of Compound 1" and HPMC.

With regard to the "crystals of Compound 1", unpulverized "crystals of Compound 1" (having a crystallinity of 87.2%), which were obtained by the process described in Japanese Published Unexamined Patent Application No. 040,652/97, was used.

Sample A was prepared in such a manner that the unpulverized "crystals of Compound 1" (10 g) and HPMC were dissolved in dichloromethane in a ratio as shown in Table 1, the solvent was distilled away and the resulting solid was pulverized for 1 minute at a rotational speed of 10,000 rpm by using a tablet pulverizer (YM-100; manufactured by Yuyama Seisakusho).

Sample B was prepared by mixing the unpulverized "crystals of Compound 1" (100 g) with HPMC in the ratio as shown in Table 1 followed by pulverizing with a pulverizer as shown in Table 1.

A physical mixture (a reference standard sample) for preparing a calibration curve was prepared by picking the unpulverized "crystals of Compound 1" and HPMC in various ratios followed by well shaking in a vinyl bag of 200×150 mm.

<Method of Measurement of a Relative Crystallinity>

The crystallinity of Compound 1 in each Sample (hereinafter, may be just referred to as the crystallinity) was calculated by the following method after measuring the diffraction peak of each Sample by changing from 0° to 40° at the angle of diffraction 2θ by a powder X-ray diffractmeter.

A calibration curve used for the calculation of the relative crystallinity was prepared by measuring the integral intensity of the diffraction peak at angle of diffraction 2θ=about 16° using physical mixtures prepared in various ratios and then plotting the ratios of amounts of the "crystalline Compound 1" in the physical mixtures against the integral intensities of the diffraction peaks respectively. Incidentally, the unpulverized "crystals of Compound 1" having a crystallinity of 87.2% was defined as the standard sample having a relative crystallinity of 100% (the "crystalline Compound 1" content was 100%), and HPMC was defined as the sample having a relative crystallinity of 0% (the "crystalline Compound 1" content was 0%).

An integral intensity of the diffraction peak of the sample at the angle of diffraction 2θ=about 16° was measured. An amount of the "crystalline Compound 1" in each sample was calculated from the measured integral intensity on the basis of the above-described calibration curve, and the relative crystallinity (%) of each sample was determined from the following formula as the ratio of the amount of "Compound 1" ("crystalline Compound 1" and "an amorphous Compound 1") against the amount of the "crystalline Compound 1". A crystallinity (%) was determined by a proportional calculation from the relative crystallinity (%) determined hereinabove and the crystallinity (87.2%) of the unpulverized "crystals of Compound 1".

Relative Crystallinity (%)=(Amount of the "crystalline Compound 1"/Amount of "Compound 1")×100

<Method for Measurement of Photostability>

Photostability of each sample was traced by measuring the residual ratio (%) of "Compound 1" in the sample according to the following method.

Transparent glass vials, in which the samples were weighed and filled, were stored at about 5,000 lx under a fluorescent lamp, and each sample was sampled 8 hours after the irradiation. The sampled sample was dissolved in a mixed solvent of water and acetonitrile (water:acetonitrile=60:40), and then the amount of "Compound 1" in the sample was determined quantitatively by using a high-performance liquid chromatography (HPLC). Amount of "Compound 1" before irradiation was defined as 100% and the amount of "Compound 1" after irradiation thereto was calculated as the residual ratio (%).

Crystallinity (%) of Samples A and B and residual ratio (%) of "Compound 1" are shown in Table 1 and correlation between the crystallinity and the stability is shown in FIG. 1.

Conditions for the measurement by HPLC are as follows.

Instrument for analysis: Series LC-6 (manufactured by Shimadzu)

Column: Inertsil ODS-2 (φ6×150 mm)

Column temperature: 25° C.

Mobile phase: 50 mmol/L $KH_2PO_4$ (pH 6.1, KOH)/acetonitrile=60/40

Flow rate: 1.2 mL/minute

Detecting condition: UV 248 nm

TABLE 1

| Names of Samples | Ratio by Weight (Non-Ground "Crystals of Compound 1":HPMC) | Pulverizer Used | Crystallinity (%) | Residual Rate of "Compound 1"(%) |
|---|---|---|---|---|
| Sample A | 1:2 | — | 68.9 | 98.6 |
| Sample A | 1:3 | — | 22.7 | 78.5 |
| Sample A | 1:5 | — | 0.0 | 23.0 |
| Sample A | 1:9 | — | 0.0 | 62.7 |
| Sample B | 1:2 | Jet Mill | 79.8 | 111.0 |
| Sample B | 1:3 | Jet Mill | 57.9 | 99.2 |
| Sample B | 1:4 | Jet Mill | 56.7 | 106.5 |
| Sample B | 1:10 | Jet Mill | 37.8 | 100.7 |
| Sample B | 1:10 | Mortar | 40.7 | 97.0 |
| Sample B | 1:10 | Mechanomill | 32.0 | 94.1 |
| Sample B | 1:10 | Ball Mill | 0.0 | 53.9 |
| Unpulverized "Crystals of Compound 1" | — | — | 87.2 | 100.0 |

As results described above, it has been found that there is a positive correlation between the crystallinity and the photostability of Compound 1 and that degradation under irradiation of light decreases when the crystallinity of the "crystals of Compound 1" is 20% or more, preferably 30% or more. Thus, it is expected that, when the crystallinity of the "crystals of Compound 1" can be kept a certain value or more during a series of steps for preparing pharmaceutical formulations such as pulverizing and dispersing or when the "crystals of Compound 1" having a crystallinity of a certain value or more can be used in the steps for preparing pharmaceutical formulations, an increase of degradation products is controlled even under irradiation of light and stability of Compound 1 in the steps for preparing pharmaceutical formulations can be maintained.

TEST EXAMPLE 2

Average Particle Size and Solubility of Crystals of Compound 1

By using Crystals A (the average particle size of crystals: 167 μm, 2 mg) and Microcrystals A (the particle size of microcrystals $D_{100}$=8.7 μm, 2 mg) obtained in Example 2, the solubility of each of them in water (200 mL) at room temperature was measured.

Solubilities (μg/mL) of Crystals A and Microcrystals A against the elapsed time are shown in FIG. 2.

As results described above, it has been found that Microcrystals A having less average particle size has quick dissolving velocity as compared to Crystals A and has a good solubility of Compound 1.

It has been also found that, in Microcrystals A, there is no phenomenon of aggregation of the crystals of Compound 1 during the operation of steps for preparing pharmaceutical formulation and that Microcrystals A have excellent dispersing property as compared to Crystals A.

TEST EXAMPLE 3

Comparison of Absorption in Oral Administration

Each of Crystal B (the average particle size of crystals: 181 μm) and Microcrystals B (the average particle size of crystals: 11 μm) obtained in Example 3 was suspended in a 0.5 w/v % aqueous solution of methyl cellulose to prepare a drug liquid (0.3 mg/mL) for administration. The resulting drug liquid was orally administered to male rats of SD strain (body weight: 209 to 233 g; Nippon Charles River) at the dose of 10 mL/kg. Blood of the rat (about 0.3 mL for each time) was sequentially collected from tail vein by using a heparin-treated capillary tube 0.25, 0.5, 1, 2, 4, 6, 8, 12 and 24 hour(s) after the administration. The resulting blood was centrifuged (1,950× g, 10 minutes, 4° C.) and plasma was separated. Concentration of "Compound 1" in the resulting plasma was measured by HPLC and mean value from three rats was calculated.

Maximum concentration in plasma ($C_{max}$), the area under the plasma curve of concentration-time curve between the administration and the point which can be determined quantitatively finally ($AUC_{0-t}$) and the area under the plasma curve of concentration-time curve between the administration and infinitive time ($AUC_{0-\infty}$), of case in which each of Crystals B and Microcrystals B were orally administered to the rat, are shown in Table 2.

Incidentally, conditions for the measurement by HPLC are as follows.

Instrument for analysis: Series L-7000 (manufactured by Hitachi)

Column: Ultron VX-ODS (φ4.6×150 mm)

Column temperature: 30° C.

Mobile phase: 10 mmol/L acetate buffer (pH 5.7)/acetonitrile=53/47

Flow rate: 1.0 mL/minute

Detecting condition: UV 360 nm

TABLE 2

| | Crystals B (mean ± s.e.m.) | Microcrystals B (mean ± s.e.m.) |
|---|---|---|
| $C_{max}$ (ng/mL) | 72.6 ± 31.7 | 238 ± 4 |
| $AUC_{0-t}$ (ng · time/mL) | 439 ± 196 | 1390 ± 240 |
| $AUC_{0-\infty}$ (ng · time/mL) | 565 ± 227 | 1530 ± 360 |

As a result described above, it has been found that, when Microcrystals B having small average particle size are orally administered, high $C_{max}$, $AUC_{0-t}$ and $AUC_{0-\infty}$ are achieved as compared with the oral administration of Crystals B, and that Microcrystals B having small average particle size has better absorption in oral administration than Crystals B.

Figure 1:
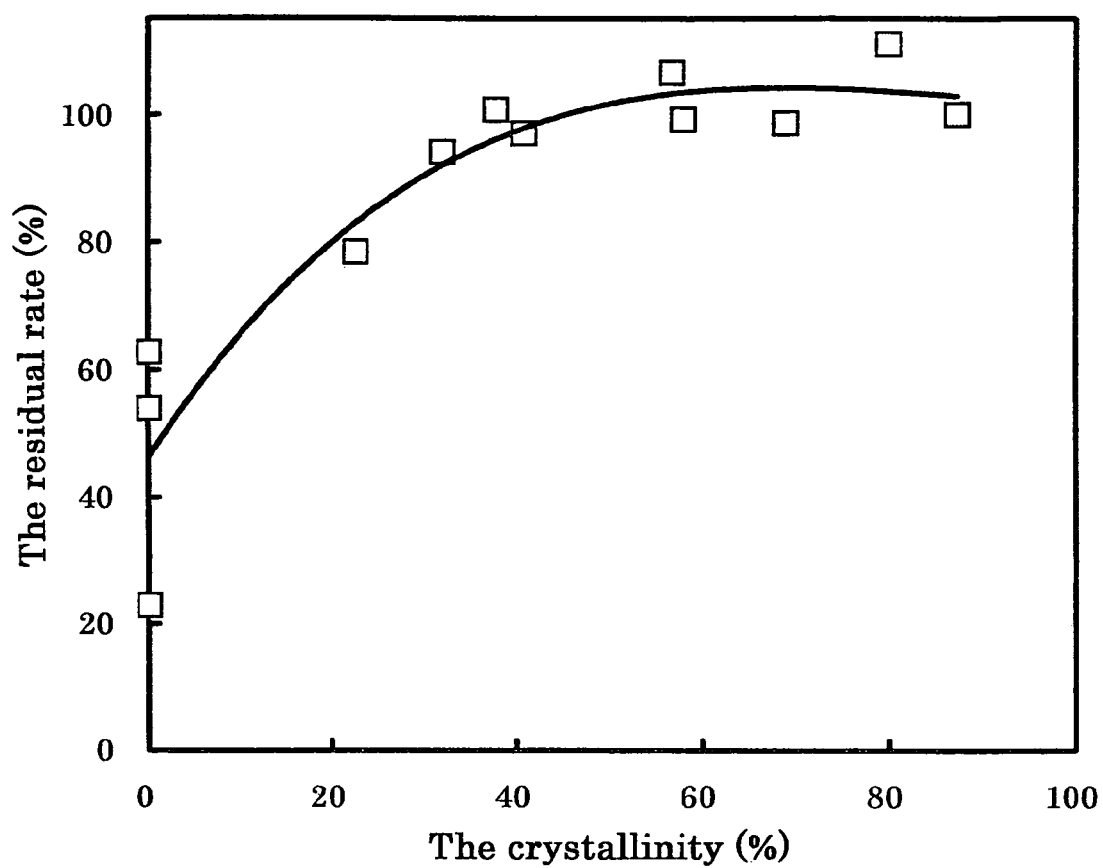
FIG. 1 shows the correlation between the crystallinity of Compound 1 in the sample of Test Example 1 and the photostability of Compound 1. The ordinate shows the residual rate (%) of Compound 1 and the abscissa shows the crystallinity (%) of Compound 1 in the sample.
Figure 2:
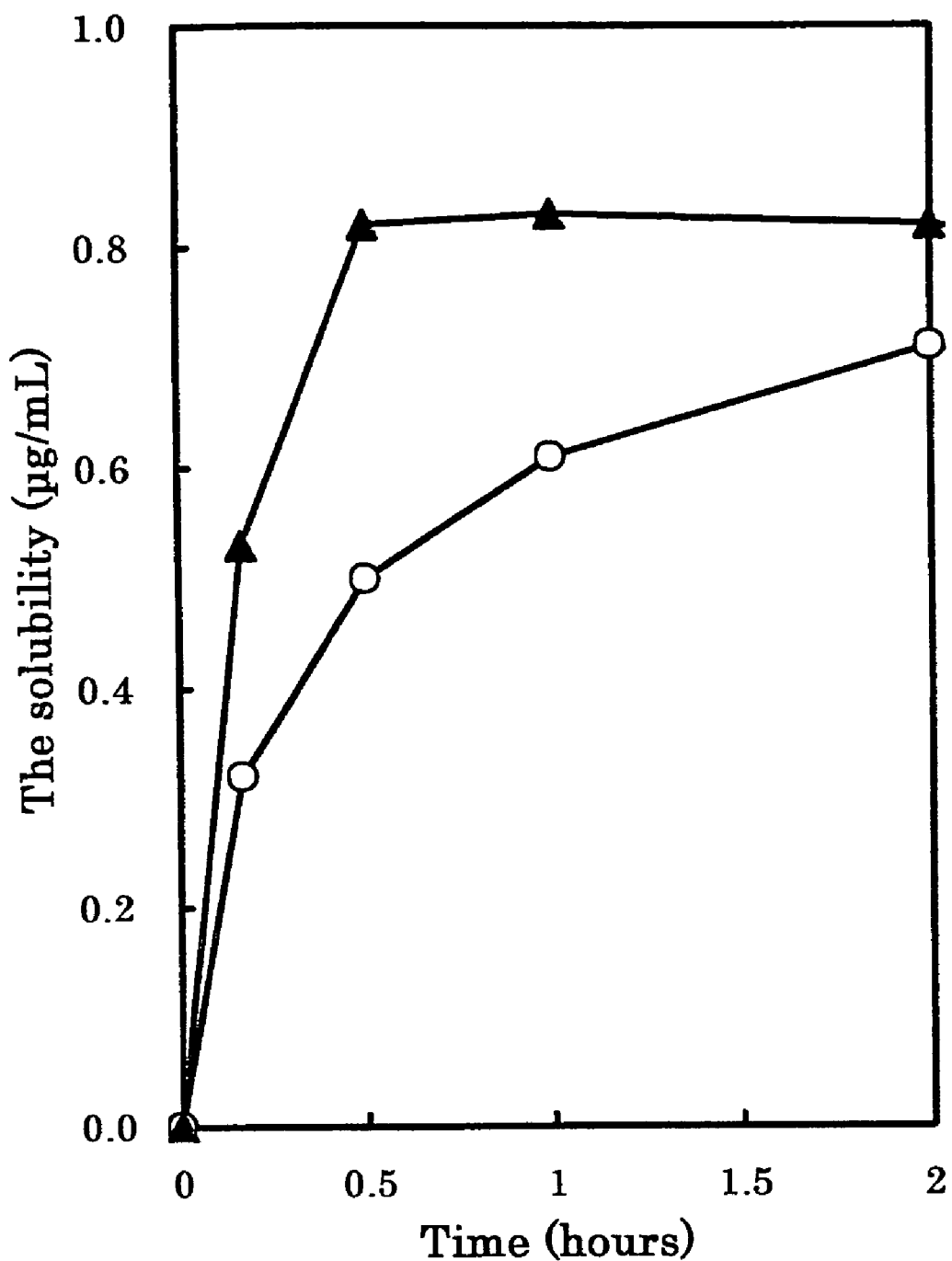
FIG. 2 shows the relation between the average particle size of the crystals of Compound 1 and the solubility of Compound 1. The ordinate shows the solubility (μg/mL) of Compound 1 and the abscissa shows the elapsed time (hours) Meanings of the plots on the graph are as follows.

-○-: the solubility of Crystals A (μg/ml)
-▲-: the solubility of Microcrystals A (μg/mL)

BEST MODE FOR CARRYING OUT THE INVENTION

The present invention is described in more detail in the following Examples. However, these Examples never limit the present invention.

EXAMPLE 1

"Crystals of Compound 1" (1 kg) was poured into a jet mill (PJMI-1.5; manufactured by Nippon Newmatic) and pulverized under pressure of 0.4 MPa while feeding at rate of 50 g/minute to obtain "microcrystals of Compound 1" (950 g) having an average particle size of 24 μm. Incidentally, the average particle size was measured by an image analyzer (Image Command 5098; manufactured by Olympus Optical; wet method).

EXAMPLE 2

Unpulverized "crystals of Compound 1" (Crystals A; an average particle size of the crystals=167 μm) was obtained by the process described in Japanese Published Unexamined Patent Application No. 040,652/97. The above-described Crystals A was pulverized by a jet mill (PJMI-1.5; manufactured by Nippon Neamatic) under pressure of 0.4 MPa while feeding at a rate of 50 g/minute to obtain "microcrystals of Compound 1" (Microcrystals A; a particle size of the microcrystals $D_{100}$=8.7 μm which means that 100% of the particles are 8.7 μm or less; a crystallinity: 84.6%). Incidentally, the average particle size was measured by an image analyzer (Image Command 5098; manufactured by Olympus Optical; wet method).

EXAMPLE 3

Unpulverized "crystals of Compound 1" (Crystals B; an average particle size of the crystals=181 μm; a crystallinity: 71.6%) was obtained by the process described in Japanese Published Unexamined Patent Application No. 040,652/97. The above-described Crystals B was pulverized by a jet mill (PJM-100SP; manufactured by Nippon Newmatic) under pressure of 0.25 MPa while feeding at a rate of 50 g/minute to obtain "microcrystals of Compound 1" (Microcrystals B; an average particle size of the crystals: 11 μM; a crystallinity: 67.3%). Incidentally, the average particle size was measured by an image analyzer (Luzex® AP; manufactured by Nicole).

EXAMPLE 4

Tablets (1)

| | |
|---|---|
| Microcrystals of Compound 1 produced in Example 1 | 40 mg |
| Lactose | 110 mg |
| Crystalline cellulose | 44 mg |
| Polyvinylpyrrolidone | 4 mg |
| Magnesium stearate | 2 mg |

The above-listed substances were mixed and compressed by a general method.

EXAMPLE 5

Capsules

| | |
|---|---|
| Microcrystals of Compound 1 produced in Example 1 | 10 mg |
| Lactose | 60 mg |
| Corn starch | 27 mg |
| Polyvinylpyrrolidone | 2 mg |
| Magnesium stearate | 1 mg |

The above-listed substance were mixed, granulated by a general method and filled in a hard gelatin capsule.

INDUSTRIAL APPLICABILITY

The present invention provides crystals of Compound 1, which possess, for example, excellent solubility, stability absorbability, dispersing property in a pharmaceutical formulation or the like, and a solid pharmaceutical formulation comprising the crystals.

The invention claimed is:

1. Microcrystals of (E)-8-(3,4-dimethoxystyryl)-1,3-diethyl-7-methyl-3,7-dihydro-1H-purine-2,6-dione represented by the following formula

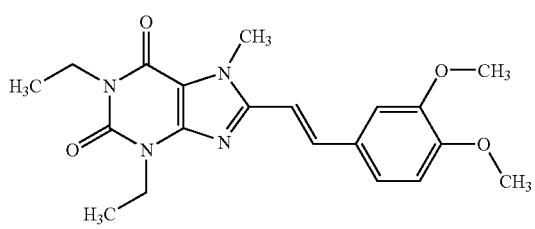

wherein the average particle size of the microcrystals is less than 50 μm.

2. The microcrystals according to claim 1, wherein the average particle size of the microcrystals is 0.5 to 20 μm.

3. A solid pharmaceutical formulation comprising the microcrystals according to claim 1 or 2, and a pharmaceutically acceptable carrier.

4. The microcrystals according to claim 1 or 2, which are obtained by pulverization using a jet mill of crystals of (E)-8-(3,4-dimethoxystyryl)-1,3-diethyl-7-methyl-3,7-dihydro-1H-purine-2,6-dione, said crystals having an average particle size of not less than 50 μm.

5. The solid pharmaceutical formulation according to claim 3, wherein the microcrystals are obtained by pulverization using a jet mill of crystals of (E)-8-(3,4-dimethoxystyryl)-1,3-diethyl-7-methyl-3,7-dihydro-1H-purine-2,6-dione, said crystals having an average particle size of not less than 50 μm.

* * * * *